US006258123B1

(12) United States Patent
Young et al.

(10) Patent No.: US 6,258,123 B1
(45) Date of Patent: *Jul. 10, 2001

(54) IOL FOR REDUCING SECONDARY OPACIFICATION

(75) Inventors: Craig Young, Presque Isle, ME (US); Glenn R. Sussman, Lake Forest; Crystal M. Cunanan, Mission Viejo, both of CA (US)

(73) Assignee: Allergan, Waco, TX (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/844,428

(22) Filed: Apr. 18, 1997

Related U.S. Application Data

(62) Division of application No. 08/627,723, filed on Apr. 2, 1996, now Pat. No. 5,693,094, which is a division of application No. 08/437,656, filed on May 9, 1995, now Pat. No. 5,549,670.

(51) Int. Cl.⁷ ..................................................... A61F 2/16
(52) U.S. Cl. ..................... 623/6.16; 623/6.17; 623/66.1
(58) Field of Search ........................ 623/6, 6.16, 6.17, 623/6.3, 66.1

(56) References Cited

U.S. PATENT DOCUMENTS

| 2,043,840 | 6/1936 | Singer . | |
|---|---|---|---|
| 3,034,403 | 5/1962 | Neefe . | |
| 3,454,332 | 7/1969 | Siegel | 351/162 |
| 4,429,421 | * 2/1984 | Levy | 623/6 |
| 4,435,856 | 3/1984 | L'Esperance | 623/6 |
| 4,449,257 | 5/1984 | Koeniger | 623/6 |
| 4,451,938 | 6/1984 | Kelman | 623/6 |
| 4,601,722 | 7/1986 | Kelman | 623/6 |
| 4,605,409 | 8/1986 | Kelman | 123/6 |
| 4,676,791 | 6/1987 | Lemaster et al. | 623/6 |
| 4,702,244 | 10/1987 | Mazzocco | 623/6 |
| 4,743,254 | 5/1988 | Davenport | 623/6 |

(List continued on next page.)

FOREIGN PATENT DOCUMENTS

| 0246754 | 11/1987 | (EP) . |
| 0457553 | 11/1991 | (EP) . |
| 0458508 | 11/1991 | (EP) . |
| 2661816 | 11/1991 | (FR) . |
| 2181355 | 4/1987 | (GB) . |
| WO93204 | 10/1993 | (WO) . |

OTHER PUBLICATIONS

Effect of posterior chamber intraocular lens design and surgical placement on postoperative outcome, Martin et al Cataract Refract Surg., vol. 18, Jul. 1992.

Spreading and Orientation of Epithelial Cells on Grooved Substrata, Brunette, Experimental Cell Research 167 (1986) 203–217.

The Rayner Choyce Mark VIII Anterior Chamber Implant, Catalogue number 469, rec'd. in PTO Jul. 31, 1978.

*Primary Examiner*—Paul B. Prebilic
(74) *Attorney, Agent, or Firm*—Stout, Uxa, Buyan & Mullins, LLP; Frank J. Uxa

(57) ABSTRACT

An IOL implantable in an eye comprising an optic having an optical portion for directing light toward the retina of the eye and a cell barrier portion for inhibiting cell growth from the eye in front of or in back of the optical portion. The cell barrier portion circumscribes the optical portion, is incapable of focusing light on the retina and includes an irregularly configured structure, for example, irregular grooves. At least one elongated fixation member is coupled to the optic for use in fixing the optic in the eye.

19 Claims, 4 Drawing Sheets

U.S. PATENT DOCUMENTS

| | | |
|---|---|---|
| 4,808,181 | 2/1989 | Kelman .................................... 623/6 |
| 5,002,571 | 3/1991 | O'Donnel, Jr. et al. ................. 623/6 |
| 5,011,494 | 4/1991 | von Recum et al. .................. 623/11 |
| 5,074,876 * | 12/1991 | Kelman .................................... 623/6 |
| 5,076,684 | 12/1991 | Simpson et al. ..................... 623/6 X |
| 5,089,023 | 2/1992 | Swanson .................................. 623/6 |
| 5,108,428 * | 4/1992 | Capecchi et al. ........................ 623/5 |
| 5,366,501 * | 11/1994 | Langerman .............................. 623/6 |
| 5,370,687 | 12/1994 | Poler ....................................... 623/6 |
| 5,405,385 | 4/1995 | Heimke et al. .......................... 623/6 |
| 5,549,670 * | 8/1996 | Young et al. ............................ 623/6 |
| 5,693,094 * | 12/1997 | Young et al. ............................ 623/6 |
| 5,713,956 * | 2/1998 | Legeais ................................... 623/5 |
| 6,129,759 * | 10/2000 | Chambers ........................... 623/6.17 |

* cited by examiner

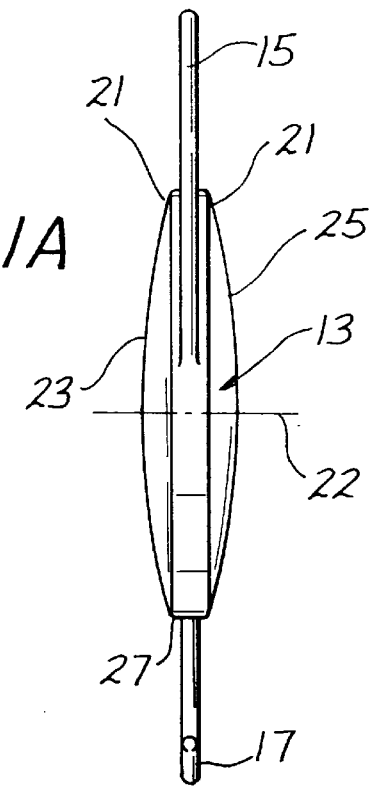
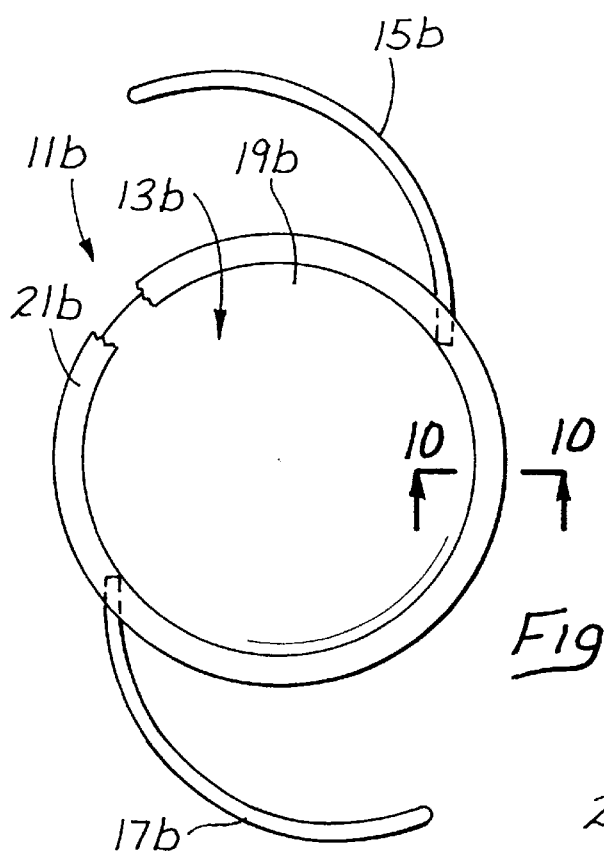
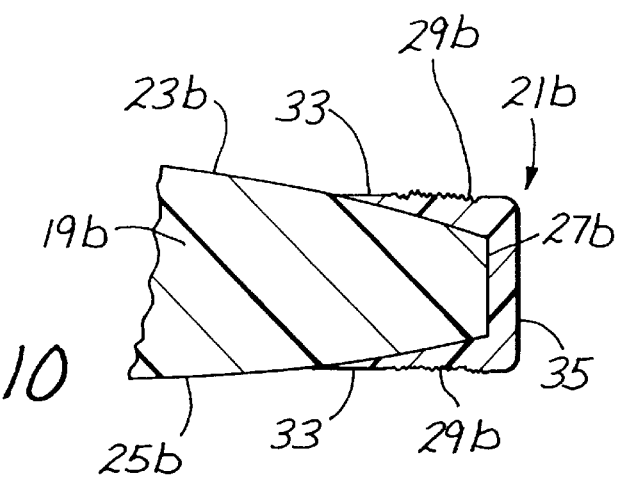

IOL FOR REDUCING SECONDARY OPACIFICATION

This is a division of application Ser. No. 08/627,723, filed Apr. 2, 1996, now U.S. Pat. No. 5,693,094, which is a division of application Ser. No. 08/437,656, filed May 9, 1995, now U.S. Pat. No. 5,549,670.

BACKGROUND OF THE INVENTION

This invention relates to intraocular lenses and in particular to intraocular lenses (IOL's) which reduce secondary opacification.

An intraocular lens is commonly used to replace the natural lens of the human eye when warranted by medical conditions. It is common practice to implant an IOL in a region of the eye known as the capsular bag or posterior capsule.

One problem that is experienced with many IOL's following their implantation is that cells from the eye, particularly lens epithelial cells from the capsular bag, tend to grow on the capsular bag in front of and/or in back of the optical portion of the IOL. This tends to block the optical portion of the IOL and to impair vision.

A common treatment for this condition is to use a laser to destroy the cells and a central region of the capsular bag. Although this treatment is effective, the laser is expensive and is not available throughout the world. There is also cost associated with the laser treatment as well as some patient inconvenience and risk of complications. Finally, the laser treatment may affect the performance of some IOL's.

Davenport U.S. Pat. No. 4,743,254 discloses an IOL which includes glare reducing sections on the opposite sides of an optic. These glare reducing sections are fully or partially opaque and their surfaces are not smooth. It has been observed that cell migration across the glare reducing sections appears to be reduced. A similar result has been observed in a plate IOL in which a plate, which is used as a haptic for fixing the IOL in the eye, surrounds the optic. Specifically cell migration across the plate, which has a somewhat textured surface, appears to be reduced.

Kelman U.S. Pat. No. 4,808,181 discloses an IOL including a lens assembly having an anterior surface formation and a posterior surface formation. At least a portion of the posterior surface formation constitutes a planar contact region adapted to seat against the posterior capsule of the eye to permanently anchor the lens assembly. The contact region is provided with a roughened surface area defined by a series of ordered narrow linear depressions extending transverse of the plane of the contact region. This patent teaches that these ordered narrow linear depressions accelerate adhesion and enhance anchoring of the tissue of the posterior capsule to the lens assembly. This patent is not concerned with secondary opacification and provides no solution to this problem.

SUMMARY OF THE INVENTION

This invention provides an IOL which is believed to solve the secondary opacification problem discussed above. With this invention, an optical portion, which is adapted to be placed in the capsular bag of an eye, directs light toward the retina of the eye, and a cell barrier portion circumscribes the optical portion. With this construction, the optical portion serves the normal function of directing and focusing light at or near the retina. The cell barrier portion inhibits cell growth from the eye, for example, from the capsular bag, in front of and/or in back of (behind) the optical portion. The optical portion and the cell barrier portion may be considered as being portions of the optic.

The cell barrier portion of the optic circumscribes the optical portion so as to not leave any path available for the migration of cells in front of or in back of the optical portion. The cell barrier portion is constructed so as to be incapable of or ineffective in focusing light on the retina. The cell barrier portion is preferably partially or wholly opaque to eliminate light scattering.

At least one fixation member, preferably an elongated fixation member, is coupled to, and preferably extends outwardly from, the optic for use in fixing the optic in the eye. Viewed from a different perspective, a structure other than the cell barrier portion is employed for fixing the optic in the eye. Such structure may include one or more fixation members of various different configurations coupled to the optic. The fixation members may be separate members attached to the optic or members which are integral with the optic, and they may comprise elongated filaments or one or more wider plate or plate-like members.

The cell barrier portion may be of any construction which performs the function of inhibiting cell growth from the eye in front of or in back of the optical portion. In this regard, the cell barrier portion may include an irregularly configured structure or surface feature, such as an irregularly roughened or textured surface region and/or one or more annular grooves which are at least partially defined by irregular surfaces.

As used herein, the terms "irregular" or "irregularly" refer to a thing, for example, an irregularly roughened surface region, or series of things, for example, irregular surfaces, which do not have a consistent order, pattern or configuration. In one embodiment, these terms refer to a thing or series of things which are substantially unordered or which have a pattern or configuration with a significant or substantial degree of randomness, or even substantially complete randomness. With particular regard to the annular groove or grooves described herein, the irregular surfaces which at least partially define, preferably which define a major portion of and more preferably which substantially completely define, such groove or grooves are represented by other than straight lines, for example, other than straight lines having a length more than about 0.001 mm or about 0.0005 mm, with the groove or grooves viewed in axial cross-section, that is in cross-section along a plane which includes the central optical axis of the optical portion. The annular grooves are not to be considered regular simply because they are present in a concentric array with each groove being substantially equally spaced apart from the adjacent groove or grooves. In one embodiment, the irregularity in accordance with the present invention is sufficient to result in the irregularly configured structure, present in an otherwise optically clear cell barrier portion to be at least about 50% opaque (that is frosty or hazy), more preferably at least about 80% opaque and still more preferably substantially completely opaque.

The irregularly configured structure or surface feature of the cell barrier portion preferably has a radial dimension of no more than about 2 mm, more preferably no more than about 0.75 mm and still more preferably no more than about 0.25 mm. If the cell barrier portion includes an annular groove, the groove preferably has a maximum width and a maximum depth each no greater than about 0.02 mm. In one preferred construction, the cell barrier portion includes at least about 20 annular grooves.

The optic has anterior and posterior faces. The irregularly configured structure, for example, surface roughening or texturing and/or grooves, may be provided on any surface or surfaces along which the cells may migrate and completely circumscribes the optical portion. Preferably, the irregularly configured structure is provided at least on the posterior face and/or anterior face of the optic in the cell barrier portion.

The irregularly configured structure or surface feature can be included in/on the cell barrier portion using any suitable technique or methodology, of course, it is important that this structure or surface feature be sufficiently irregular to achieve the desired inhibition of cell migration or cell growth so that the risk of secondary opacification is reduced. The technique or methodology chosen to include this structure or surface feature should take this basic criterion into account. This structure or surface feature can be formed during the initial formation, for example, the molding, of the cell barrier portion or optic, or can be included after the cell barrier portion or optic is produced, for example, using a laser, lathe, other mechanical implement and the like. In one particularly useful embodiment, a lathe is employed to form a spiral array of annular grooves defined by irregular surfaces in the cell barrier portion. Cell barrier portions may be processed in a manner similar to the glare reducing sections of Davenport U.S. Pat. No. 4,743,254 to yield fully or partially opaque structures the surfaces of which are irregular and not smooth. The disclosure of this patent is incorporated in its entirety herein by reference.

The cell barrier portion may be integral with the optical portion, or may be a separate member coupled to the optical portion. Also, the fixation member or members may be integral with the cell barrier portion and/or the optical portion, or may be a separate element or elements, e.g., filament or filaments, coupled to the optical portion or the cell barrier portion.

The invention, together with additional features and advantages thereof may best be understood by reference to the following description taken in connection with the accompanying illustrative drawings.

BRIEF DESCRIPTION OF THE DRAWINGS

FIG. 1A is an elevational view of the IOL shown in FIG. 1.

FIG. 9 is a plan view with portions broken away of a third from of IOL constructed in accordance with the teachings of this invention.

FIG. 10 is an enlarged fragmentary sectional view taken generally along line 10—10 and illustrating another construction of the cell barrier portion.

DESCRIPTION OF THE PREFERRED EMBODIMENTS

Figure 1:
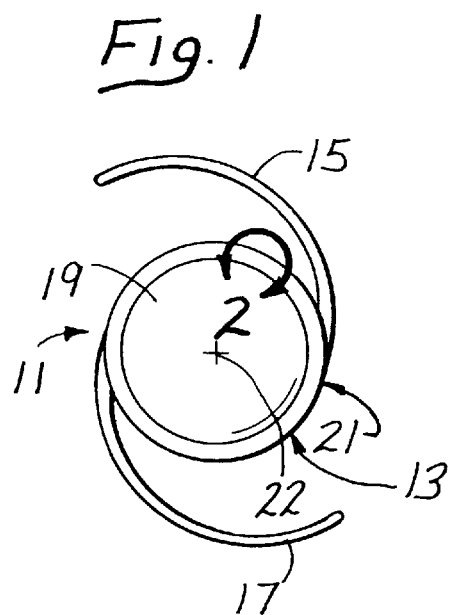
FIG. 1 is a plan view of one form of IOL constructed in accordance with the teachings of this invention.
Figure 2:
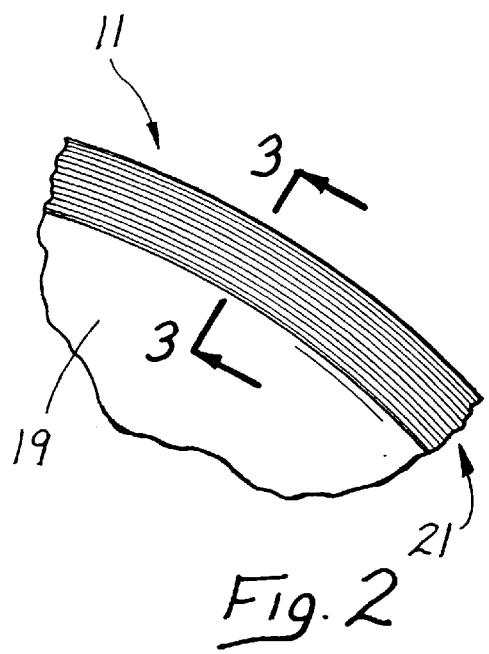
FIG. 2 is an enlarged fragmentary view of the region generally bounded by the arc 2 in FIG. 1 and showing a more detailed view of the cell barrier portion of the IOL.
Figure 3:
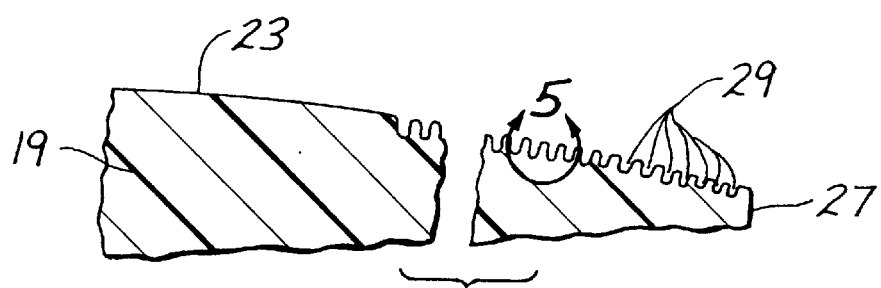
FIG. 3 is an enlarged fragmentary sectional view taken generally along 3—3 of FIG. 2.

FIGS. 1 and 1A show an IOL 11 which generally comprises an optic 13 and fixation members 15 and 17. In this embodiment, the optic 13 may be considered as including an optical portion 19 for focusing light on or near the retina of the eye and a cell barrier portion 21 circumscribing the optical portion and being incapable of focusing light on the retina. Optical axis 22 passes through the center of optic 13 in a direction generally transverse to the plane of the optic.

In this embodiment, the optic 13 is circular in plan and biconvex; however, this is purely illustrative as other configurations and shapes may be employed. The optic 13 may be constructed of any of the commonly employed materials commonly used for rigid optics, such as polymethylmethacrylate (PMMA), or commonly used for resiliently deformable optics, such as silicone polymeric materials, acrylic polymeric materials, hydrogel-forming polymeric materials, mixtures thereof and the like.

The fixation members 15 and 17 in this embodiment are generally C-shaped and are integral with the optic 13. However, this is purely illustrative as the fixation members 15 and 17 may be of other configurations and/or may be separate members affixed to the optic in any of a variety of conventional ways.

The optic 13 has an anterior face 23, a posterior face 25 and a peripheral edge 27. In this embodiment, the faces 23 and 25 are convex and the peripheral edge 27 is cylindrical, but as indicated above, these shapes are shown only by way of example.

The optic 13 is designed to be placed in the capsular bag. The diameter of the optic 13 may be conventional, and as such, may be about 6 mm or less. The optical portion 19 performs the normal function of the optic of an IOL, i.e. to appropriately focus light at or near the retina. The optical portion 19 may be monofocal or multifocal.

Figure 4:
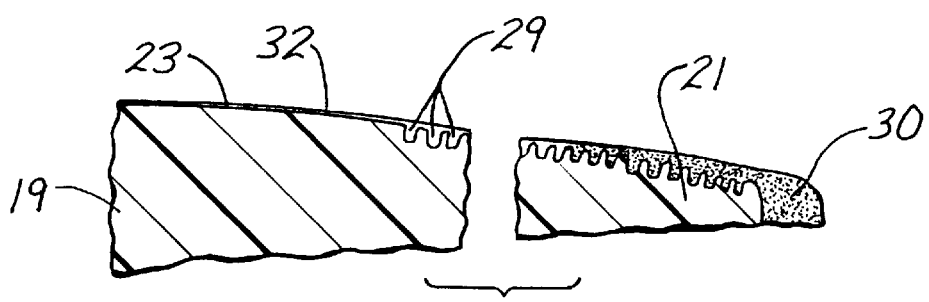
FIG. 4 is an enlarged fragmentary sectional view taken generally along line 3—3 of FIG. 2 and showing the growth of cells from the capsular bag of the eye on only a portion of the cell barrier region.
Figure 5:
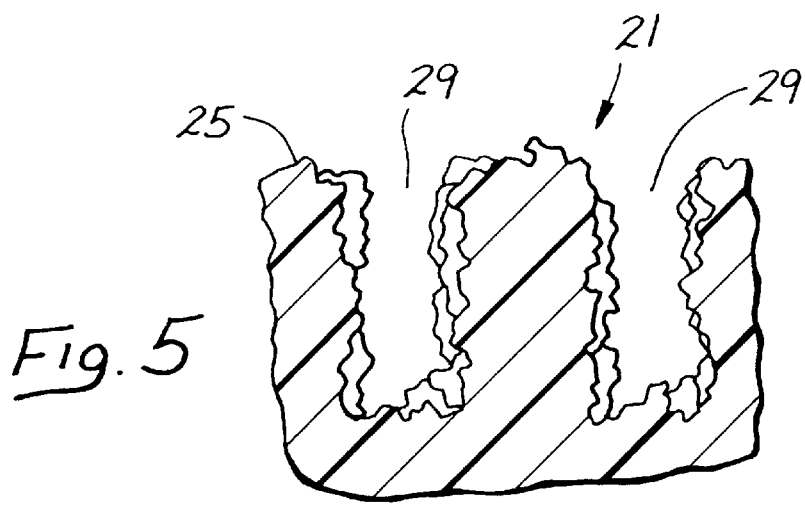
FIG. 5 is an enlarged fragmentary view of the region generally identified by the line 5—5 in FIG. 3 and showing the substantial irregularity of the grooves of the cell barrier portion.
Figure 6:
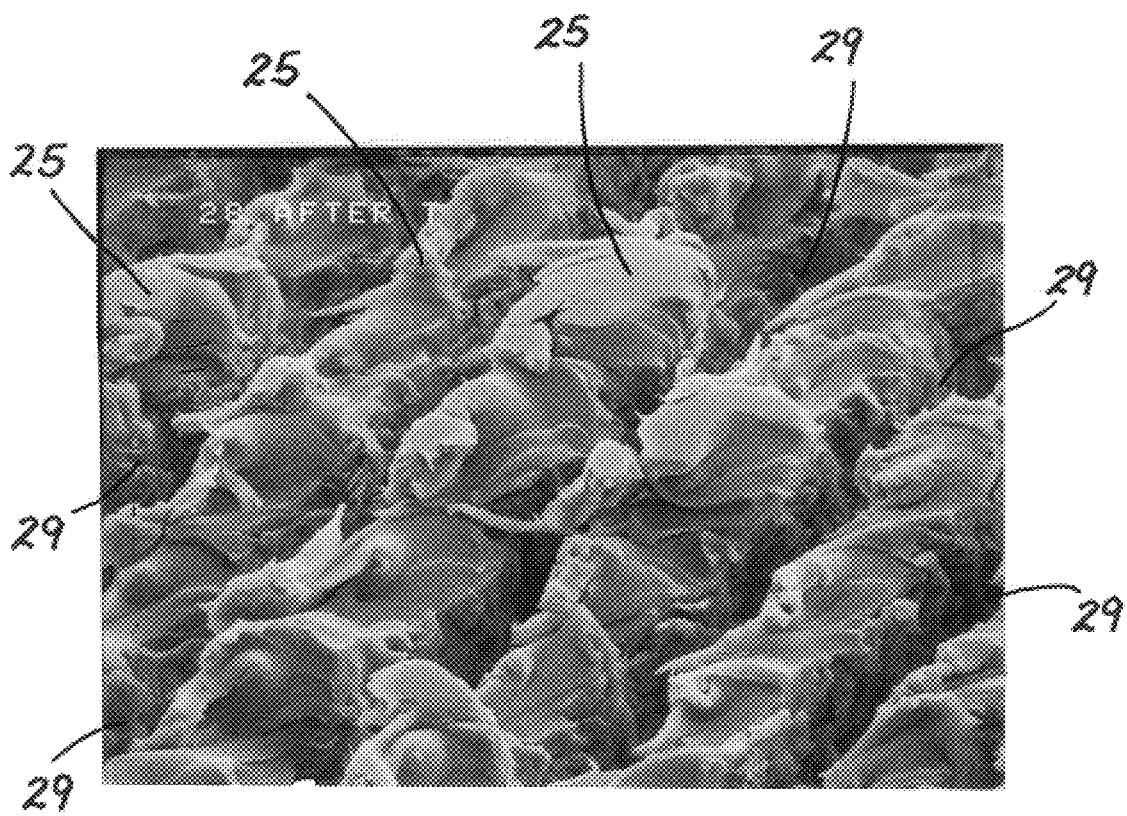
FIG. 6 is a photograph of a portion of a cell barrier portion of an IOL in accordance with the present invention at 1000 times magnification and showing the irregular annular grooves.

In this embodiment, the cell barrier portion 21 is integral with the optical portion 19. For example, as shown in FIGS. 1 to 4. cell barrier portion 21 is unitary with optical portion 19 and is made of the same material as is optical portion 19. The cell barrier portion 21 is incapable of focusing light on the retina of the eye and includes an irregularly configured structure or surface feature effective to inhibit, and preferably substantially prevent, cell growth radially inwardly across the cell barrier portion. In the embodiment of FIGS. 1–6, the cell barrier portion 21 includes a concentric array of annular grooves 29 each of which is at least partially defined by irregular surfaces. Similar arrays of the grooves 29 are in both the anterior face 23 and the posterior face 25. Although various different arrangements can be employed, in this embodiment the grooves 29 are concentric and substantially equally spaced apart. Each of the grooves 29 has sufficient irregularity in its structure so as to at least inhibit migration of cells across the groove. For this purpose, each of the grooves 29 has a maximum depth of no more than about 0.02 mm and a maximum width at the face 23 (or face 25 as the case may be) of no more than about 0.005 mm or about 0.01 mm or about 0.02 mm. In addition, the grooves 29 are substantially completely defined by irregular surfaces. In particular, each of the grooves 29 is represented by other than straight lines having a length more than about 0.001 mm, with the groove viewed in axial cross-section along a plane which includes the optical axis 22. This irregularity of grooves 29 is illustrated in detail in FIG. 5. FIG. 6 is a photograph of a number of the grooves 29 which demonstrate their substantial irregularity.

Without wishing to limit the invention to any particular theory of operation, it is believed that the irregularly configured structure of cell barrier portion 21, for example, grooves 29, acts to disrupt or otherwise interfere with the process of eye cell, for example, lens epithelial cell, migration or growth so that the cumulative effect of this irregular structure is to significantly reduce, or even eliminate, the migration or growth of cells in front of or in back of the optical portion 19 after IOL 11 is implanted in the eye. FIG. 4 illustrates that eye cells 30 from the capsular bag 32 do migrate or grow to some extent onto and cover a portion of the cell barrier portion 21. This limited cell migration is advantageous in at least assisting or facilitating the effective fixation of IOL 11 in the eye. Thus, the present invention preferably provides for such advantageous limited eye lens epithelial cell migration or growth while preventing excessive cell migration or growth in front of or in back of the optical portion 19, as shown in FIG. 4.

Another way of viewing the degree of irregularity of the irregularly configured structure, for example, grooves 29, on cell barrier portion 21 is opacity. The grooves 29 are sufficiently irregular so that the cell barrier portion 21 is substantially completely opaque to the transmission of light. When viewed by the naked eye, cell barrier portion 21 is a white or frosty band on the otherwise optically clear optic 13.

The irregularity of grooves 29 is in contrast to the regular or ordered grooves of the prior art, for example, the linear ordered grooves disclosed in Kelman U.S. Pat. No. 4,808,181. The Kelman grooves are defined as being ordered whereas the present grooves, such as grooves 29, are defined by irregular, even randomly or unordered, surfaces, as described elsewhere herein. Under 1000 times magnification, the Kelman grooves are still defined (in axial cross-section) by straight lines. FIGS. 5 and 6 show that grooves 29, in accordance with the present invention, are not defined (in axial cross-section) by straight lines. Also, although the region of the Kelman IOL which includes the linear ordered grooves may be somewhat distorted (not totally optically clear), this region still remains substantially transparent to the passage of light. In contrast, the present grooves 29 and cell barrier portion 21 are substantially opaque to the transmission of light. As noted above, the irregularity of the present cell barrier portion is an important aspect of the present invention in inhibiting the migration of eye cells onto the optical portion of the optic and clearly distinguishes the present IOLs from prior art IOLs, such as the IOLs of Kelman U.S. Pat. No. 4,808,181 and the like IOL which included regular or ordered surface grooves and the like features.

Preferably, the radial dimension of the cell barrier portion 21 is no greater than about 2 mm, and more preferably no greater than 0.25 mm. In the embodiment shown in FIGS. 1 to 6, the spacing between the grooves 29 along the face 23 may be about 0.005 mm to about 0.02 mm and the radial spacing between the outermost groove 29 and the peripheral edge 27 may be about 0.02 mm to about 0.1 mm.

In the embodiment shown in FIGS. 1 to 6, the number of grooves 29 is about 50 to about 100. In order to obtain an advantageous degree of cell migration inhibition, it is preferred that the number of grooves included in cell barrier portion 21 be at least about 20, although fewer grooves can provide some useful benefits.

The grooves 29 are located wherever it is desired to inhibit cell migration. In the present embodiment, the grooves 29 are placed on both the anterior face 23 and the posterior face 25 so that the cell barrier portion 21 is on both faces of the optic 13. However, the cell barrier portion can be eliminated from a particular face if it is determined that cell migration in front of that face is not likely to occur.

The IOL 11 can be implanted in the capsular bag of the eye in accordance with conventional techniques. When so implanted, the cell barrier portion 21 defines a radially relatively narrow annular barrier for inhibiting cell growth radially inwardly in front of or in back of the optical portion 19 where the cells could cause secondary opacification.

The present invention is applicable to IOLs including a hard or rigid optic, such as the optics made from PMMA, and those which include a foldable or deformable optic, such as optics comprising silicone polymeric materials, other acrylic polymeric materials, hydrogel-forming polymeric materials, such as polyhydroxyethylmethacrylate (poly HEMA), and the like. Such foldable/deformable optics are particularly advantageous since they can be inserted into the eye through a small incision. The fixation members 15 and 17, are flexible and strandlike or filaments so that they can be easily inserted into the eye. The fixation members 15 and 17 can be formed integrally with the optic 13 or can be separately coupled to the optic.

Figure 7:
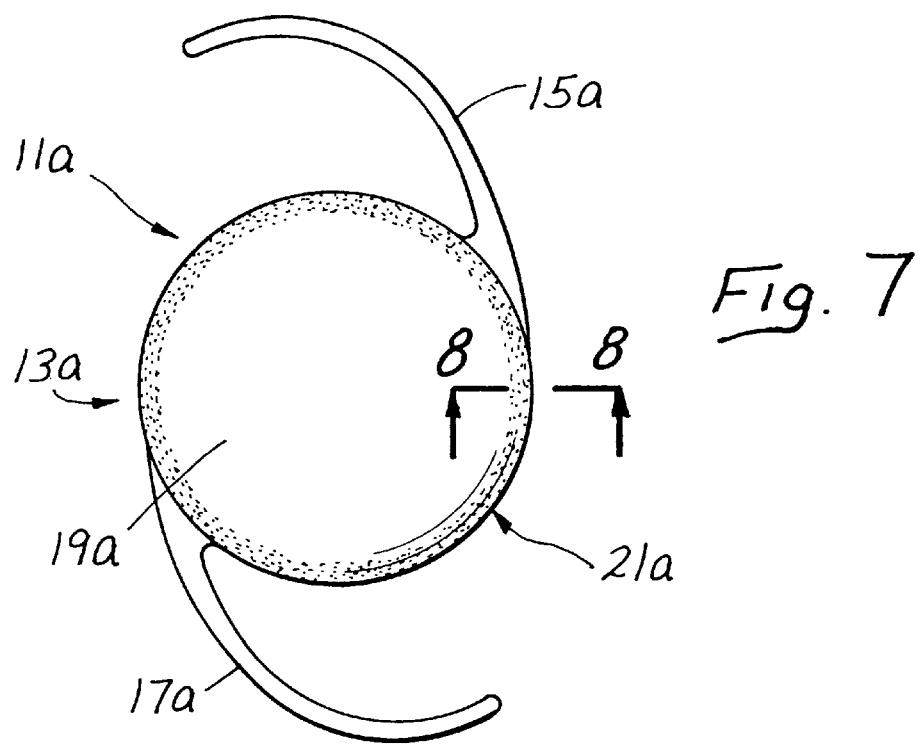
FIG. 7 is a plan view of a second form of IOL constructed in accordance with the teachings of this invention.
Figure 8:
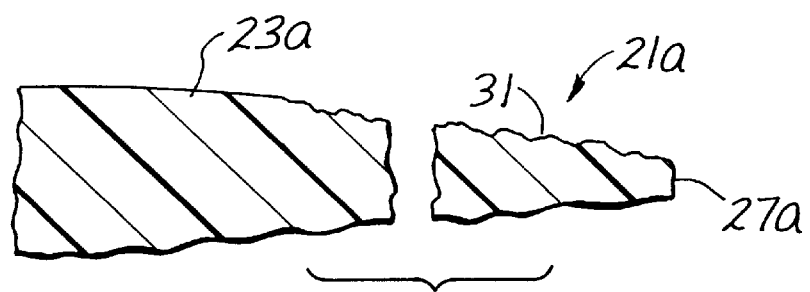
FIG. 8 is an enlarged fragmentary sectional view taken generally along line 8—8 of FIG. 7.

FIGS. 7 and 8 show an IOL 11a which is identical to the IOL 11 in all respects not shown or described herein. Portions of the IOL 11a corresponding to portions of the IOL 11 are designated by corresponding reference numerals followed by the letter a.

The only difference between the IOL's 11 and 11a is that in the IOL 11a the grooves 29 are replaced with an irregularly roughened or textured surface 31. The cell barrier portion 21a, in particular the roughened or textured surface 31, is sufficiently irregular as to be at least partially, and preferably substantially completely, opaque to the transmission of light. This not only provides cell migration inhibition, but also avoids glare from the interaction of light with the cell barrier portion 21a. The textured surface 31 may be textured or roughened in any of a variety of ways including machining as with a lathe, chemical etching, abrading or the like. If the optic 13a is molded, as for example when it is constructed of silicone polymeric material or other soft foldable material, the texturing or roughening of the textured surface 31 may be imparted by the mold.

The degree of irregularity of the roughening of the surface 31 should be sufficient to enable the textured surface to perform the inhibition of cell migration function.

FIGS. 9 and 10 show an IOL 11b which is identical to the IOL 11 in all respects not shown or described herein. Portions of the IOL 11b corresponding to portions of the IOL 11 are designated by corresponding reference numerals follows by the letter b.

There are two primary differences between the IOL's 11b and 11. First, in the IOL 11b, the fixation members 15b and 17b are separate strands or filaments which are attached to the optic 13b in an suitable conventional manner. Secondly, the cell barrier portion 21b is in the form of a separate member coupled to the optical portion 19b.

In this embodiment, the cell barrier 21b includes spaced legs 33 joined by a web 35. The legs 33 engage the faces 23b and 25b, respectively, and the web 35 confronts and engages the peripheral edge 27b. The cell barrier portion 21b is annular and extends completely around the optical portion 19b and is mounted on the optical portion in a manner similar to a tire. The cell barrier portion 21b may have a radial width of up to about 2 mm or about 1 mm, for example, about 0.25 mm.

While this invention has been described with respect to various specific examples and embodiments, it is to be understood that the invention is not limited thereto and that it can be variously practiced within the scope of the following claims.

What is claimed is:

1. An intraocular lens implantable in an eye comprising:
   an optical portion adapted for placement in a capsular bag of the eye and for directing light toward the retina of the eye;
   a cell barrier portion circumscribing said optical portion and being incapable of focusing light on the retina, and said optical portion and said cell barrier portion being made of the same material, said cell barrier portion structured to be at least about 50% opaque and white when viewed by a naked eye; and
   at least one elongated fixation member coupled to said optical portion or said cell barrier portion and extending radially outwardly of said optical portion and said cell barrier portion for fixing said intraocular lens in the eye.

2. The intraocular lens of claim 1 wherein said cell barrier portion is at least partially opaque.

3. The intraocular lens of claim 1 wherein said cell barrier portion is effective to inhibit cell growth from the eye in front of and/or in back of said optical portion.

4. The intraocular lens of claim 1 wherein said cell barrier portion is effective to inhibit migration of cells from the eye in front of and/or in back of said optical portion.

5. The intraocular lens of claim 1 wherein said cell barrier portion includes at least about 20 annular grooves each of which is at least partially defined by irregular surfaces.

6. The intraocular lens of claim 1 wherein said cell barrier portion has a radial dimension of no more than about 2 mm.

7. An intraocular lens implantable in an eye comprising:
   an optical portion adapted for placement in a capsular bag of the eye and for directing light toward the retina of the eye;
   a cell barrier portion made of a polymeric material, circumscribing said optical portion, and structured to be at least partially opaque and white when viewed by a naked eye; and
   at least one elongated fixation member coupled to said optical portion or said cell barrier portion and extending radially outwardly of said optical portion and said cell barrier portion for fixing said intraocular lens in the eye.

8. The intraocular lens of claim 7 wherein said cell barrier portion is at least 50% opaque.

9. The intraocular lens of claim 7 wherein said cell barrier portion is at least 80% opaque, said polymeric material being selected from the group consisting of polymethylmethacrylate, silicone polymeric materials, other acrylic polymeric materials, hydrogel-forming polymeric materials and mixtures thereof.

10. The intraocular lens of claim 7 wherein said cell barrier portion is effective to inhibit cell growth from the eye in front of and/or in back of said optical portion.

11. The intraocular lens of claim 7 wherein said cell barrier portion is effective to inhibit migration of cells from the eye in front of and/or in back of said optical portion.

12. An intraocular lens implantable in an eye comprising:
    an optical portion adapted for placement in the capsular bag of the eye and for directing light toward the retina of the eye; and
    a cell barrier portion circumscribing said optical portion and being structured to be effective to inhibit cell growth from the eye in front of and/or in back of said optical portion, said cell barrier portion includes an array of annular grooves each of which is at least partially defined by irregular surfaces.

13. The intraocular lens of claim 12 wherein said cell barrier portion is effective to inhibit migration of cells from the eye in front of and/or in back of said optical portion.

14. The intraocular lens of claim 12 wherein said cell barrier portion is at least 50% opaque.

15. The intraocular lens of claim 12 wherein said cell barrier portion is at least 80% opaque, and said intraocular lens further comprises at least one elongated fixation member coupled to said optical portion or said cell barrier portion for use in fixing said intraocular lens in the eye.

16. An intraocular lens implantable in an eye comprising:
    an optical portion adapted for placement in a capsular bag of the eye and for directing light toward the retina of the eye; and
    a cell barrier portion made of a polymeric material, circumscribing said optical portion and being structured to be effective to inhibit migration of cells from the eye in front of or in back of said optical portion, said cell barrier portion further being structured to be at least partially opaque and white when viewed by a naked eye.

17. The intraocular lens of claim 16 wherein said cell barrier portion is at least 50% opaque, and said polymeric material being selected from the group consisting of polymethylmethacrylate, silicone polymeric materials, other acrylic polymeric materials, hydrogel-forming polymeric materials and mixtures thereof.

18. The intraocular lens of claim 16 wherein said cell barrier portion is at least 80% opaque.

19. The intraocular lens of claim 16 wherein said cell barrier portion has a radial dimension of no more than about 2 mm.

* * * * *

UNITED STATES PATENT AND TRADEMARK OFFICE
CERTIFICATE OF CORRECTION

PATENT NO.    : 6,258,123 B1
DATED         : July 10, 2001
INVENTOR(S)   : Craig Young et al.

It is certified that error appears in the above-identified patent and that said Letters Patent is hereby corrected as shown below:

<u>Column 3,</u>
Line 10, "methodology, of" should read -- methodology. Of --.

<u>Column 7,</u>
Lines 30-31, claim 2 should be deleted.

Signed and Sealed this

Second Day of September, 2003

JAMES E. ROGAN
*Director of the United States Patent and Trademark Office*